US008398400B2

(12) United States Patent
Bondar

(10) Patent No.: US 8,398,400 B2
(45) Date of Patent: Mar. 19, 2013

(54) PICK-UP IMPLANT ABUTMENT AND METHOD

(76) Inventor: Vitali Bondar, Portsmouth, NH (US)

( * ) Notice: Subject to any disclaimer, the term of this patent is extended or adjusted under 35 U.S.C. 154(b) by 74 days.

(21) Appl. No.: 12/676,087

(22) PCT Filed: Sep. 9, 2008

(86) PCT No.: PCT/US2008/075695
§ 371 (c)(1),
(2), (4) Date: Mar. 2, 2010

(87) PCT Pub. No.: WO2009/035968
PCT Pub. Date: Mar. 19, 2009

(65) Prior Publication Data
US 2010/0248180 A1 Sep. 30, 2010

Related U.S. Application Data

(60) Provisional application No. 60/993,694, filed on Sep. 12, 2007.

(51) Int. Cl.
*A61C 13/12* (2006.01)
*A61C 13/225* (2006.01)
*A61C 8/00* (2006.01)

(52) U.S. Cl. ........................................ 433/172; 433/173

(58) Field of Classification Search .......... 433/172–176, 433/201.1, 213–214, 141, 146, 147; 29/239
See application file for complete search history.

(56) References Cited

U.S. PATENT DOCUMENTS

| 5,106,300 | A | * | 4/1992 | Voitik | 433/173 |
|---|---|---|---|---|---|
| 5,362,234 | A | * | 11/1994 | Salazar et al. | 433/169 |
| 5,376,004 | A | * | 12/1994 | Mena | 433/173 |
| 5,538,426 | A | * | 7/1996 | Harding et al. | 433/172 |
| 5,674,072 | A | * | 10/1997 | Moser et al. | 433/173 |
| 6,168,463 | B1 | * | 1/2001 | Wu | 439/567 |
| 6,726,481 | B1 | * | 4/2004 | Zickmann et al. | 433/173 |
| 6,932,606 | B2 | * | 8/2005 | Aravena et al. | 433/173 |
| 2004/0063069 | A1 | * | 4/2004 | Lombardi | 433/173 |
| 2005/0181331 | A1 | * | 8/2005 | Lustig et al. | 433/173 |
| 2005/0233281 | A1 | * | 10/2005 | Gittleman | 433/173 |
| 2006/0084033 | A1 | * | 4/2006 | Gittleman | 433/173 |
| 2008/0032263 | A1 | * | 2/2008 | Bondar | 433/173 |
| 2008/0254411 | A1 | * | 10/2008 | Bondar | 433/174 |

FOREIGN PATENT DOCUMENTS

EP 1946720 * 1/2007

OTHER PUBLICATIONS

Written Opinion of International Searching Authority of International Application No. PCT/US2008/75695, Nov. 10, 2008.

* cited by examiner

*Primary Examiner* — Yogesh Patel
(74) *Attorney, Agent, or Firm* — Notaro, Michalos & Zaccaria P.C.

(57) ABSTRACT

A dental implant abutment arrangement for use with a dental implant has an abutment with a proximal retaining member and an axial bore. The retaining member is rotationally asymmetrical and has a transverse area that is large enough to resist rotation and axial motion of the abutment in a dental impression material. The axial bore has a tapered distal bore portion with an inner taper for matching an outer taper of an abutment receiving portion of an implant, a cylindrical proximal bore portion and an intermediate threaded portion having a small diameter than the distal and proximal bore portions and a larger diameter than an internal thread of the implant. The axial bore has distal and proximal steps between the distal bore portion and a distal end of the threaded portion and between the proximal bore portion and a proximal end of the threaded portion. An insertion tool is provided for pulling the abutment toward the implant to removably lock the inner taper to the matching the outer taper and a removal tool is provided for pushing the abutment away from the implant to disengage the lock between the inner taper and the outer taper.

6 Claims, 11 Drawing Sheets

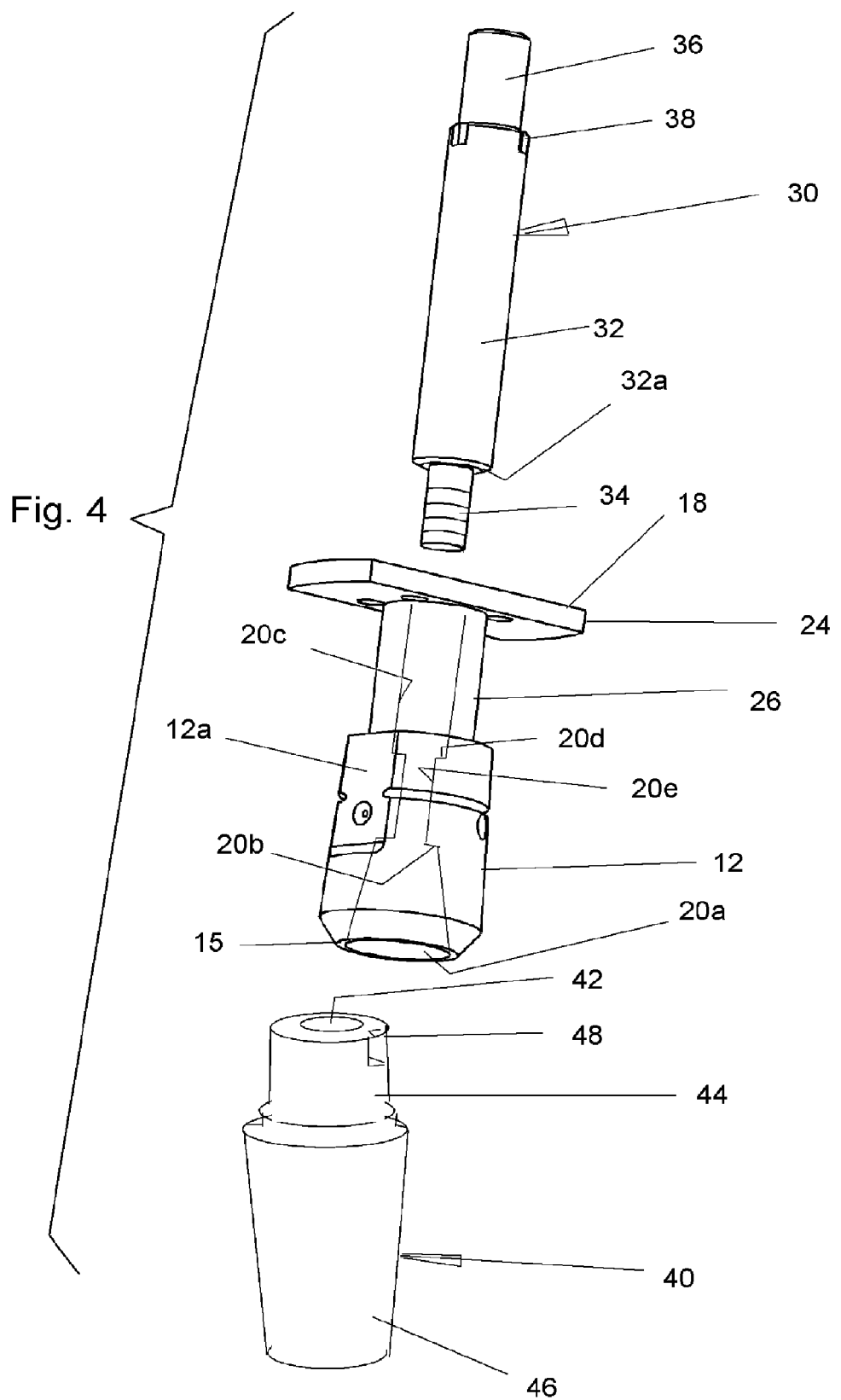

PICK-UP IMPLANT ABUTMENT AND METHOD

CROSS-REFERENCE TO RELATED APPLICATION

This application claims priority on U.S. Provisional Patent Application 60/993,694 filed Sep. 12, 2007, which is incorporated here by reference.

FIELD AND BACKGROUND OF THE INVENTION

The present invention relates generally to the field of implant dentistry, and in particular to a new and useful pick-up implant abutment.

Impression copings are used to register the position of a dental implant placed into a patient's jaw. Two types of impression copings are used for implant level indexing.

The first type of impression coping is called a transfer coping which remains on an implant after the impression material is removed from the mouth. It is then removed from the implant, attached to the implant analog and inserted back into the impression. This technique is called the "closed tray method." There are several factors which influence the accuracy of the closed tray method.

One factor is that it is impossible to machine the implant engaging parts of the impression coping and the implant abutment to be the same. A second factor is that it is impossible to machine the abutment engaging parts of the implant analog and the implant to be the same. Thirdly, some degree of impression material distortion always occurs during removal and re-insertion of the coping into the hardened impression material. This prevents accurate seating of the coping inside the impression.

A fourth factor is due to manufacturing tolerances. It is impossible to mate the implant analog with the implant abutment in exactly the same position as will be done with the implant and implant abutment later in the patient's mouth. A fifth factor is due to severe distortion of the impression material that occurs upon removal of the impression tray when multiple angulated implants are present.

The second type of implant impression or indexing is called the "open tray method" which eliminates the third and fifth factors. Impression coping used in this method is called pick-up coping, since it stays inside the impression material after the impression is removed from the mouth. The use of an elongated fastener and the hole made in the impression tray provide the means to disengage the coping from the implant and allow the removal of the impression from patient's mouth. The coping remains inside the impression material.

Though more accurate than the closed tray method, the open tray method still does not solve the three other problems noted above.

There is a need for a new abutment and method for taking an implant level impression which would eliminate the negative effect of size discrepancy between implant and implant analog, abutment and abutment analog and would also have the benefits of an open tray impression method.

The use of pick-up or transfer copings can be especially detrimental with locking taper implants (an example is described in the inventors co-pending international patent application PCT/US2007/074847 filed Jul. 31, 2007, and his U.S. patent application Ser. Nos. 11/615,131 filed Dec. 22, 2006, and 12/092,900 filed May 7, 2008) due to the sliding nature of the mating components. Discrepancies in diameter between the internal locking taper bore of the impression coping and the locking taper bore of the abutment will be multiplied several times due to sliding nature of the locking taper connection. A difference of only 6 microns will lead to a 100 microns difference in a vertical dimension (distance between the abutment or the impression coping, and the implant shoulder) between the impression coping/implant assembly and abutment/implant assembly. Current machining tolerances are much greater than 6 microns. If conventional impression methods are used, the discrepancy can be as high as 0.3 mm.

U.S. Pat. No. 5,106,300 to Voitik teaches the use of impression coping that is attached to the implant abutment and is picked up together with the abutment in the impression tray during an impression taking step. The open tray impression method is advocated by the inventor. Although more accurate then other described methods, this method also presents multiple challenges. Impression coping has to be used; impression coping has to be stocked in different sizes for abutments of different diameters and lengths; impression coping has to be properly attached to the abutment; and impression coping can separate from the abutment during impression removal because the fastener connecting the impression coping to the abutment and the implant has to be removed.

Known locking taper connection systems use conventional impression methods which produce inaccurate and unpredictable results.

An implant known as the Nobel Active external, was introduced in 2007 by Nobel Biocare AB, of Göteborg, Sweden, the largest implant manufacturer in the world. It has a 3 degree locking taper post and an indexing element in the form of a hex positioned on its end. The mating abutment has an internal 3 degree tapered bore and an internal indexing hex. The manufacturer realized that the use of impression coping would not yield an accurate result, so the standard crown and bridge impression method was advocated. The abutment is prepared by the dentist, tapped over the implant and an impression of the abutment is then taken and is sent to the laboratory for prosthesis fabrication. It is universally accepted that the use of implant level impression coping is much preferred in implant dentistry over the standard crown and bridge method.

Impladent Ltd. of Holliswood, N.Y., is an external locking taper implant manufacturer that also relies on the standard crown and bridge impression method.

The Bicon implant system (from Bicon Dental Implants of Boston, Mass.) uses implants having an internal locking taper bore and abutments with an external locking taper post. Bicon introduced the use of a plastic impression post which is tapped into the bore of the implant and is picked up by the impression material. The implant analog is than tapped over the post, and the abutment is tapped into the implant analog. During the prosthesis delivery appointment the abutment is tapped into the implant while the custom made acrylic jig restricts the rotational movement of the abutment. Many factors make accurate indexing impossible, however, the most critical ones being the inability of the operator to control tapping force and the difference in diameter between the implant analog and the implant, which affects the vertical positioning of the abutment. The abutment may seat more or less into the implant well, up to 0.1-0.2 mm, when compared to the implant analog.

It has been shown that accurate (i.e. within 0-10 microns range) repeated vertical connection between locking taper abutments and implants can only be achieved if:
 1) the same abutment is mated with the same implant; and
 2) the same amount of force is applied to activate the locking taper connection.

Accordingly a need remains for an improved pick-up implant abutment and the new method of implant position indexing that avoid the problems of the prior art.

SUMMARY OF THE INVENTION

It is an object of the present invention to provide a dental implant abutment arrangement for use with any known dental implant that has a proximal retaining member connected to the upper surface of the abutment which enables the abutment to be used as a pick-up coping during impression taking process. The retaining member is preferably rotationally asymmetrical and has a transverse area that is large enough to resist rotation and axial motion of the abutment in impression material, the angle between the connector and the retaining member being preferably close to or equal to 90 degree to prevent axial movement of the abutment in the impression material.

A further object of the invention is to provide the dental implant abutment arrangement for use with a dental implant having an anchoring portion for anchoring in a jaw bone of a patient and an abutment receiving portion opposite from the anchoring portion, the abutment receiving portion having an outer taper for removably locking to an inner taper of an abutment, indexing means incorporated into the abutment receiving portion, and an internal implant thread having diameter and a pitch. The arrangement comprises an abutment having a body with a peripheral wall and a distal end for engagement with the implant, the abutment having a proximal end with a retaining member and a connector connecting the retaining member to the body, the abutment having an axial bore there through extending between the distal and the proximal ends and having an axis, the retaining member being rotationally asymmetrical about the axis and having an area transverse to the axis that is greater than a transverse area of the connector so that the retainer resists rotation and axial motion of the abutment in an impression material for taking a dental impression, the axial bore having a tapered distal bore portion with an inner taper for matching the outer taper of the abutment receiving portion, a cylindrical proximal bore portion, and an intermediate threaded portion having a smaller diameter than that of the distal and proximal bore portions and a larger diameter than the internal thread of the implant, the axial bore having a distal step between the distal bore portion and a distal end of the threaded portion, and a proximal step between the proximal bore portion and a proximal end of the threaded portion, and the indexing means disposed distally to the threaded portion. The arrangement also includes an insertion tool having body with a diameter that is smaller than that of the cylindrical proximal bore portion so that the insertion tool can slide into the cylindrical proximal bore portion, a proximal end with anti-rotation means for engagement of the insertion tool to rotate the insertion tool, and a threaded implant engaging end having a diameter and pitch for threading into the internal thread of the implant, the threaded implant engaging end being of a smaller diameter than a remainder of the insertion tool body for defining a distal step around a proximal base of the threaded implant engaging end, the threaded implant engaging end being threaded into the internal thread of the implant for pulling the abutment toward the implant to removably lock the inner taper to the matching the outer taper as the a distal step of the insertion tool engaged the proximal step of the axial bore. The arrangement also includes a removal tool having body with a diameter that is smaller than that of the cylindrical proximal bore portion so that the removal tool can slide into the cylindrical proximal bore portion, a proximal end with anti-rotation means for engagement of the removal tool to rotate the removal tool, and a threaded abutment engaging end having a diameter and pitch for threading into the threaded portion of the axial bore, and having a diameter that is greater than the diameter of the internal thread of the implant and a length that is sufficient so that the rotation of the removal tool causes pushing of the abutment away from implant to disengage the lock between the inner taper and the outer taper as the proximal end of the removal tool engages the abutment receiving portion.

Another object of the invention is to provide an open tray impression and model making method that takes advantage of the unique features of the abutment arrangement.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 4 is an exploded side perspective view of the a locking taper pick-up abutment with an insertion tool according to the invention, and an implant for use with the invention;

DESCRIPTION OF THE PREFERRED EMBODIMENTS

For the purpose of this disclosure, relative positional terms such as "up" or "upper" or "down" or "lower" are meant to include their opposite meaning and are not limitations of the invention since the orientation will change whether upper or lower implants are involved, without departing from the principles of the invention.

Figure 1:
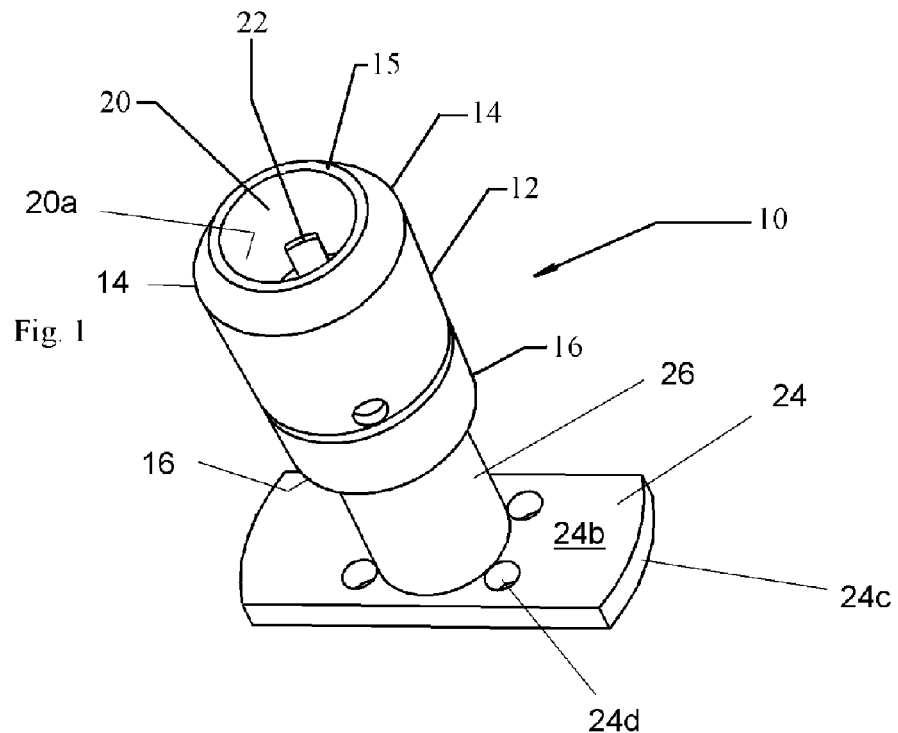
FIG. 1 is a side distal perspective view of a locking taper pick-up abutment according to the present invention.
Figure 2:
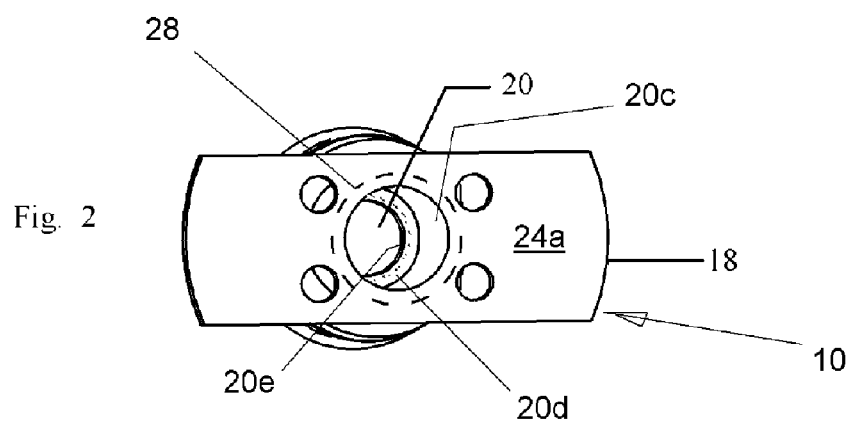
FIG. 2 is a proximal perspective view of the locking taper pick-up abutment.
Figure 3:
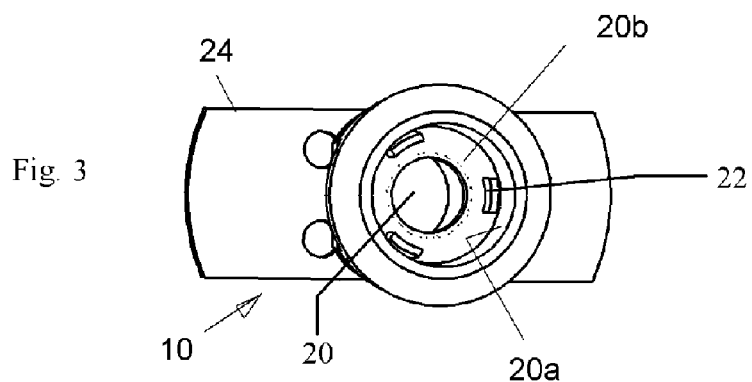
FIG. 3 is a distal perspective view of the locking taper pick-up abutment.

The Locking Taper Pick-Up Abutment:

Referring now to the drawings, in which like reference numerals are used to refer to the same or similar elements throughout, FIGS. 1, 2 and 3 illustrate a locking taper pick-up abutment 10 for use with external locking taper implants, the abutment having a body 12 with an outer peripheral wall that tapers from a large diameter location 14 near its distal end 15, to a smaller diameter intermediate location 16. The body 12 may have a different shape, however. Pick-up abutment 10 has a proximal end 18 that is opposite its distal end 15, and an axial through bore 20 that extends all the way between the distal end 15 and the proximal end 18 of the abutment 10.

The abutment 10 also has internal rotational implant indexing means located at the distal end 15, for example, one or more axial protrusions 22 or other indexing configuration, corresponding to that of an abutment receiving portion of the implant itself, to be described later in connection with FIGS. 5-7. The indexing means may alternatively be in the form of an internal hex or any other configuration that insures the correct relative rotational positions between the abutment 10 and the implant. Prosthesis anti-rotational means are provided by one or more flat surfaces 12a on the otherwise conical or cylindrical outer peripheral wall of body 12.

Figure 3A:
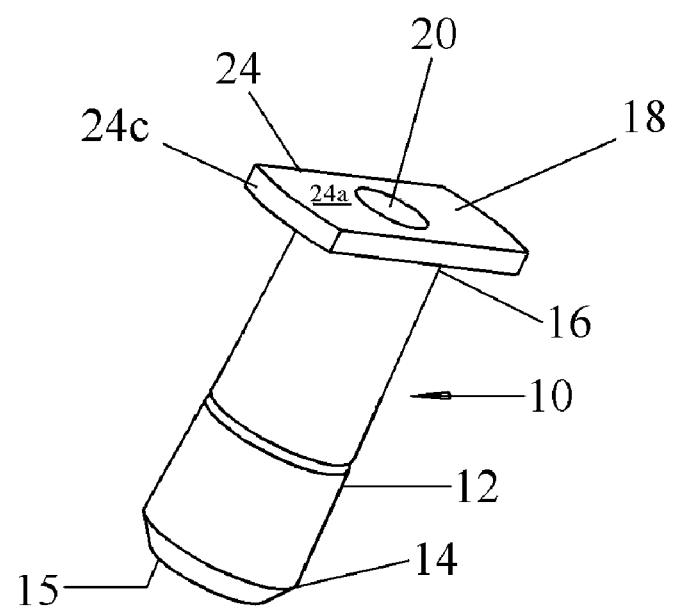
FIG. 3A is a side perspective view of a pick-up abutment embodiment.

The proximal end 18 of the abutment 10 has a retaining member 24 that is in the form of a disk or a plate or has another shape that is preferably asymmetrical. The retaining member 24 is connected to the body 12 of abutment 10, by a connector 26 that is cylindrical and has a smaller outside diameter then that of the body 12. The use of connector 26 is optional since retaining member 24 can be joined to or be a part of abutment body 12, as demonstrated in FIG. 3A. Connector 26 may have another shape as long as its transverse cross-sectional area, transverse to the axis of bore 20, is less than that of body 12. Retaining member 24 has upper (proximal) and lower (distal) surfaces 24a and 24b with an effective surface area, transverse to the axis of bore 20, that is greater than the transverse cross-sectional area of connector 26. This results in good vertical stability of the entire abutment 10 in the impression material of an impression tray to be used in accordance with a method of the present invention, during an impression removal step of the method. Retaining member 24 may contain anti-rotational features, such as the rotationally asymmetrical shape shown, to prevent rotation in the impression material. Retaining member 24 also has a selected thickness between its upper and lower surfaces, so as not to become bent or distorted during impression removal. At the same time it should not be too thick so as to facilitate removal by cutting of the retaining member away from the connector 26, for example, using a dental burr, along a cutting line or area 28 at a later stage of the method. The cutting area 28 may be circular line in the retaining member 24 that corresponds to the diameter of the connector 26, or it can correspond to a cross-section of the abutment body if the retaining member 24 is connected directly, without the connector 26, to the abutment body 12.

To this end the range of thickness for retaining member 24 is about 0.5 to 1.0 mm, or preferably about 0.7 to 0.8 mm. A preferred shape for the retaining member 24 is rectangular, and, in the embodiment shown, the rectangular shape has a longer dimension that is greater than the maximum diameter of the abutment body 12 with rounded ends 24c extending in the shorter dimension of the rectangle, the length of shorter dimension being between the diameter of the connector 26 and the minimum diameter of the abutment body 12.

The abutment 10 may be manufactured as one piece or be made of multiple permanently attached pieces.

As best shown in FIGS. 1 and 3, the axial bore 20 has a distal or lower end portion 20a that is tapered inwardly from the distal end 15, up to a distal step-down in diameter at 20b. The taper of distal bore portion 20a is selected to match the locking taper, e.g. a Morse taper of about 1 to 4 degrees, of an abutment receiving portion of an implant to be used with the abutment. As best shown in FIG. 2, axial bore 20 also includes a proximal or upper end bore portion 20c that is cylindrical and extends up along bore 20 to a proximal step-down in diameter at 20d.

Referring now to FIGS. 2, 3 and 4, axial bore 20 also includes a threaded intermediate bore portion 20e with a smaller diameter then the upper and lower bore portions 20a and 20c. Threaded bore portion 20e extends between proximal step 20d and distal step 20b of axial bore 20, which define the opposite ends of the threaded bore portion 20e.

The Locking Taper Pick-Up Abutment Arrangement:

FIG. 4 also illustrates an abutment insertion tool 30 which has an elongated body 32, a threaded implant engaging distal end 34 and a proximal end 36 with anti-rotational elements 38, such as circumferentially spaced, axial grooves at the top of body 30 for allowing application of torque using an appropriately shaped wrench or wrench engaging instrument. Threaded implant engaging distal end 34 has an external thread that corresponds in size and pitch to an internal thread 42 in a tapered abutment receiving portion 44 of an implant 40 shown also in FIGS. 5 to 7.

Treaded distal end 34 has a smaller cross section and diameter then elongated body 32 to form a step-down in diameter at a distal step 32a. Elongated body 32 is also of a small enough diameter to slide into cylindrical bore portion 20c of bore 20 and treaded end 34 is small enough to pass the threads of threaded bore portion 20e and is long enough to reach the internal threads 42 of implant 40 until distal step 32a engages proximal step 20c of bore 20 as shown in FIG. 5. Further rotation of insertion tool 30 up to a precisely selected amount of torque accurately and firmly engages the female Morse taper 20a of bore 20 with the corresponding male Morse taper of abutment receiving portion 44. In this way the locking connection between the abutment 10 and the implant 40 is achieved by apply an accurate seating force against the upper or proximal step 20d that is also at the upper end of the threaded portion 20e of the bore 20. This achieves an accurate and repeatable Morse taper locking connection that cannot be achieved by the known taping of the parts together.

Implant 40 also includes a known anchoring portion 46, such as a thread to be screwed into a bore in the patient's jaw bone, as well as the external abutment receiving portion 44 shaped to form the locking taper, indexing means in the form of an external hex, grooves 48 or any other indexing configuration and a threaded internal bore 42 of a predetermined depth at the proximal or upper end of the implant 40.

Figure 5:
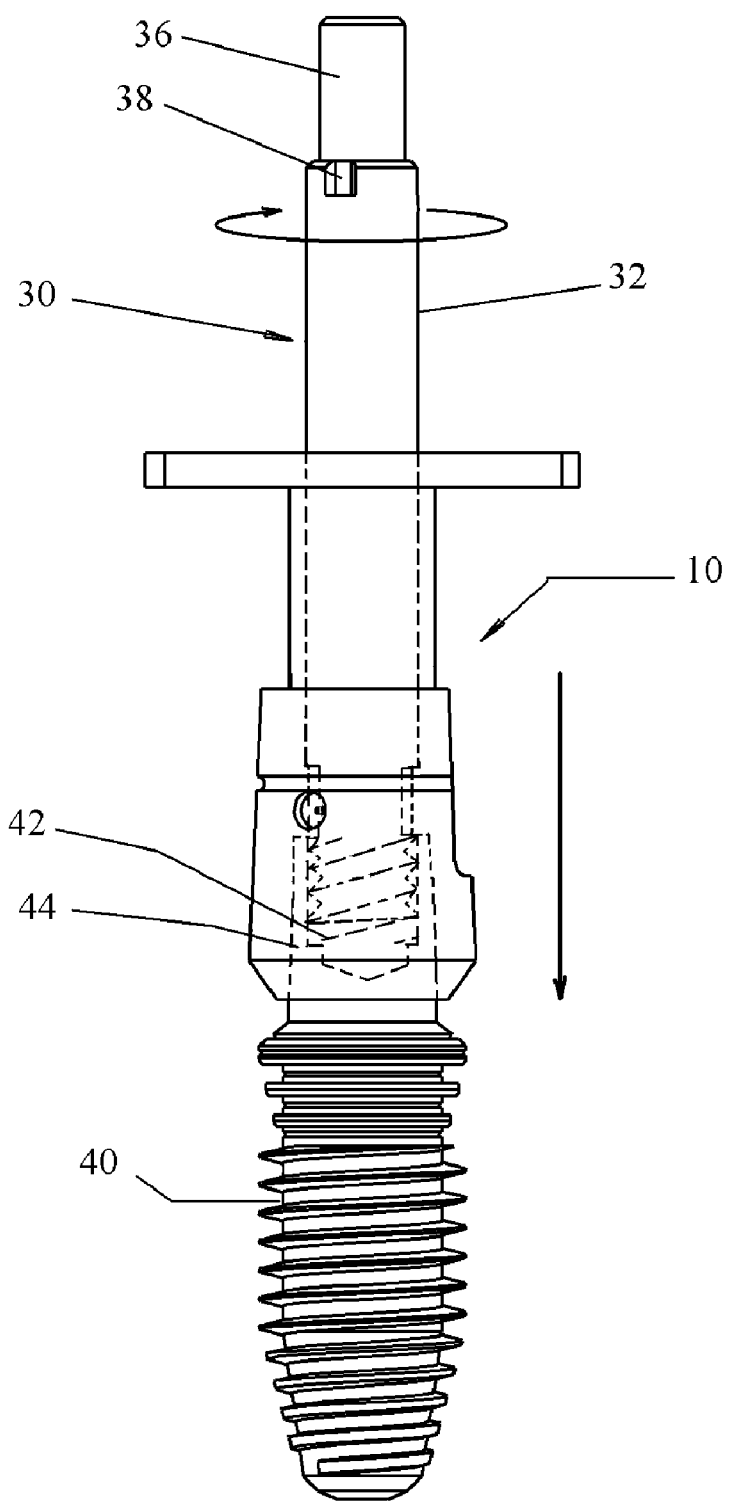
FIG. 5 is a side elevational view of a seated locking taper pick-up abutment arrangement of the present invention which includes the abutment and the insertion tool, and shows a dental implant for use with the invention.

FIG. 5 thus illustrates the arrangement of the invention including the abutment 10 that is adapted to be connected to the implant 40, and the insertion tool 30 for achieving the accurate locking.

Figure 6:
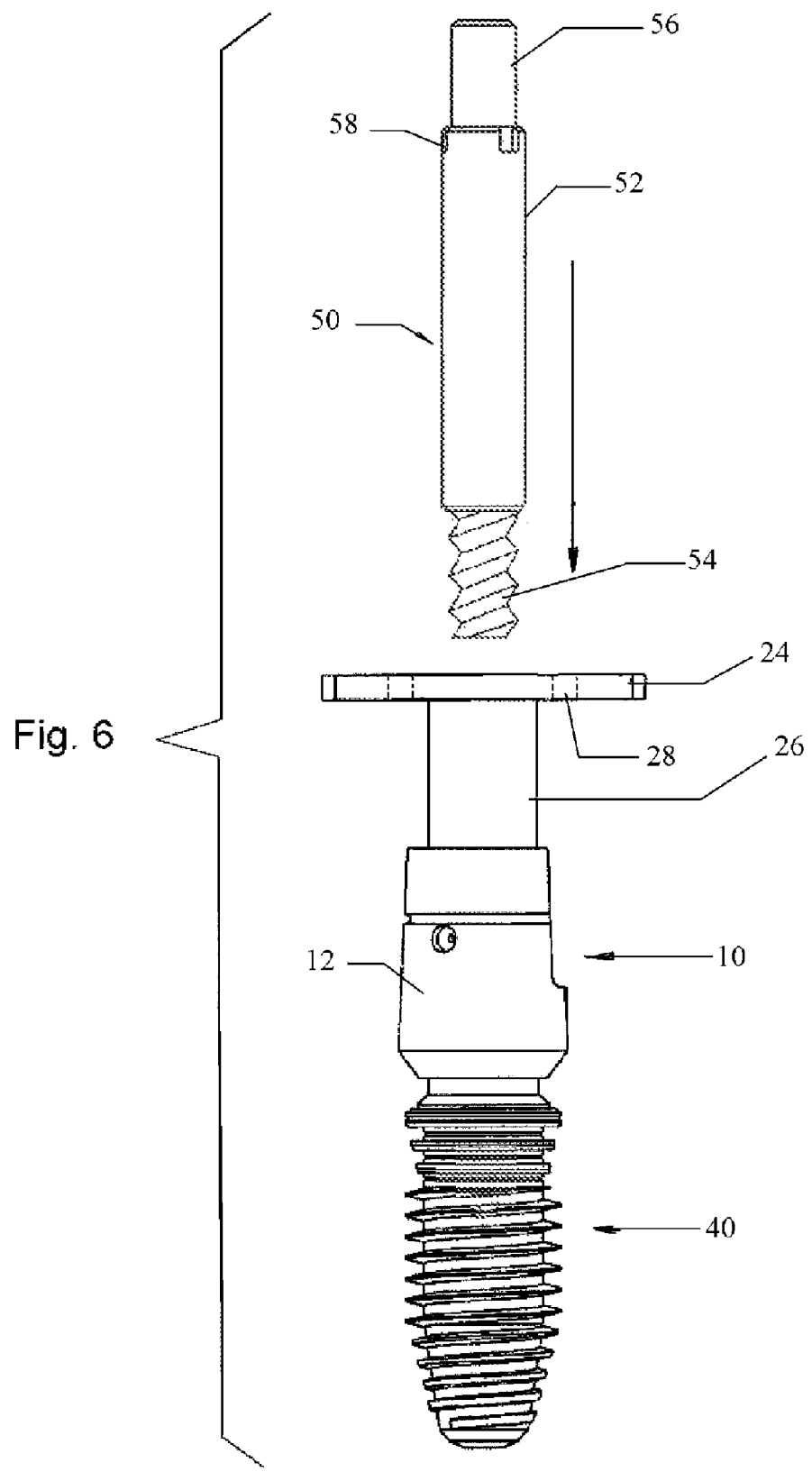
FIG. 6 is a side elevational and exploded view of a locking taper pick-up abutment arrangement of the present invention which includes the abutment, a removal tool and shows an example of the dental implant to be used with the invention.
Figure 7:
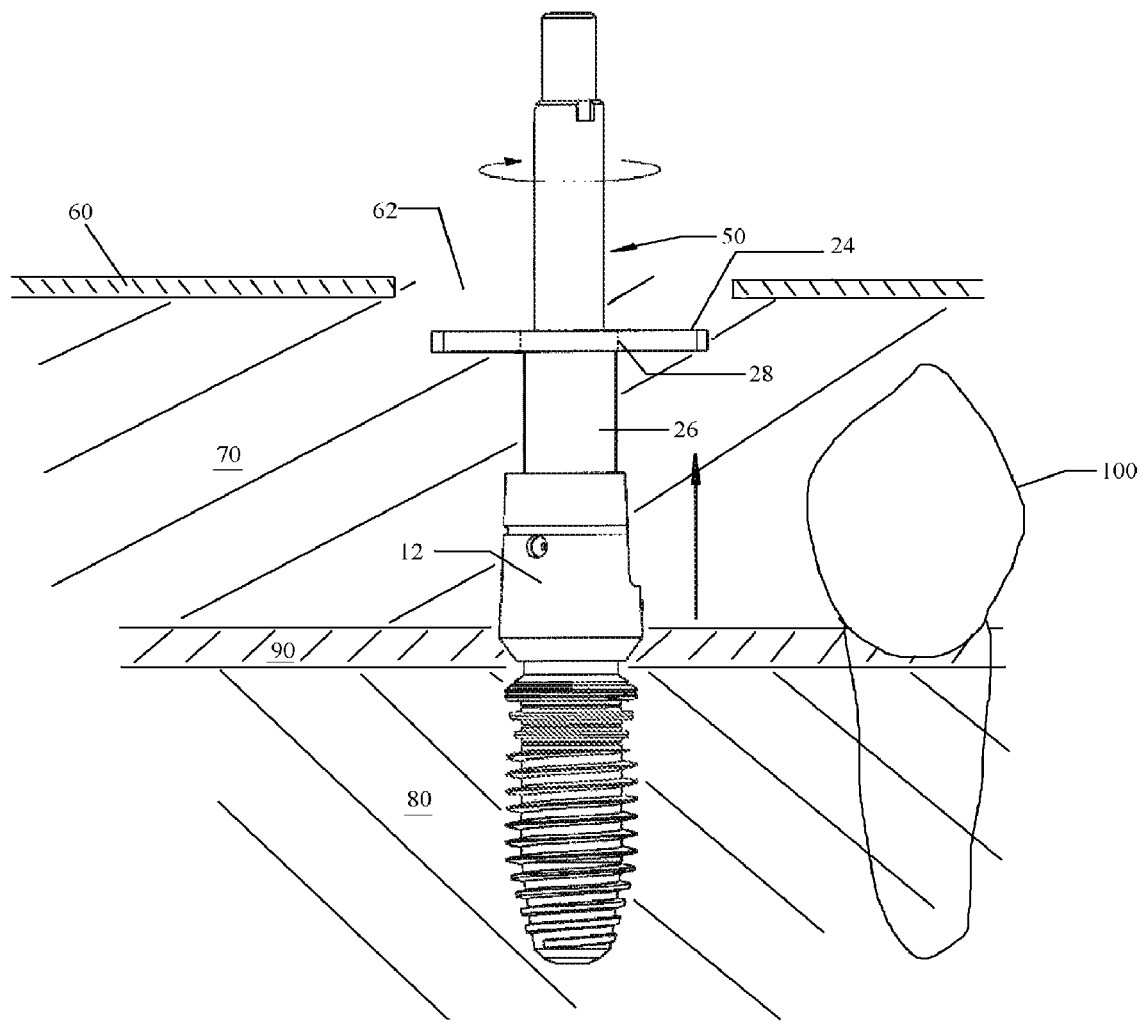
FIG. 7 is a side elevational view of the locking taper pick-up abutment arrangement of FIG. 6, during rotation of the removal tool to disconnect the abutment from the dental implant and with the arrangement in an impression material while practicing the method of the invention.

FIGS. 6 and 7 illustrate an additional removal tool 50 that is used in combination with the abutment 10, the implant 40 and, for the earlier phase of the method of the invention, the insertion tool 30, that together form an overall arrangement of the present invention. Since various known implants may be used with a suitably adapted abutment 10 and tools 30 and 50 of the invention, the implant itself need not be a part of the arrangement of the invention.

Abutment removal tool 50 has an elongated body 52, a threaded distal abutment engaging end 54 extending distally, and a proximal end 56 with anti-rotational elements 58 that, like elements 38 of the insertion tool 30, allow for the application of torque using a wrench to rotate the tool 50. Threaded distal abutment engaging end 54 has an external thread that corresponds in size and pitch to the threaded bore 20e of axial bore 20 of the abutment 10. With the diameter of elongated body 52 being small enough to allow tool 50 to slide into the proximal cylindrical bore portion 20c of bore 20, and the threaded end 54 being longer than threaded intermediate portion 20e, tool 50 is rotated to screw threaded end 54 into the full length of treaded portion 20e and to emerge past lower distal step 20b at the lower or distal end of the threaded bore portion 20e. Threaded end 54 has a larger diameter than the internal implant thread 42 so that as tool 50 continues to rotate, the distal end of treaded end 54 presses distally (downwardly in FIGS. 6 and 7) against the implant and disengages the abutment 10 from abutment receiving portion 44 of the implant 40 to unlock the Morse tapers from each other. This rotation and disengagement action is illustrated in FIG. 7.

In the embodiment of FIGS. 1-7 the connecting means for connecting the abutment 10 with its retaining member 24, to the abutment receiving portion 44 are the engaged Morse taper surfaces and the tool 30. Disengagement is accomplished with tool 50.

Before and after this disengagement occurs, however, other steps of the method of the invention can be practiced, as will now be explained.

The Pick-Up Abutment Method for Locking Taper Implant Systems:

The invention includes a method of taking a dental impression utilizing the pick-up abutment and locking taper implant as described above. The method takes an open tray impression of an oral arch of a patient having at least one dental implant in the patient's jaw bone.

As shown in FIG. 5, locking taper connection is activated between the abutment 10 and abutment receiving portion 44 of the implant with the help of tool 30 and, as described above, calibrated torque wrench set to deliver precise amount of force. This type of connection does not rely on retaining screw to hold abutment and the implant together. Tool 30 is removed from abutment 10.

As shown in FIG. 6, tool 50 is screwed into the threaded bore 20e of the abutment 10 using only light finger force, since disengagement of locking taper surfaces is not desired at this moment.

An impression tray shown schematically as 60 in FIG. 7, has an opening 62 to allow tool 50 to protrude out through impression material 70 and out of the tray. The impression tray 60 with impression material 70 is inserted over the implant 40 that is in the patient jaw bone 80 under gum 90, and over the surrounding dentition shown schematically at 100. Opening 62 preferably has larger cross-section than retaining member 24 to allow for slight compression of the impression material 70.

Alternatively, tool 30 can be left inside abutment 10 while impression material 70 and tray 60 are inserted over abutment 10. Tool 30 is removed after impression material is hardened and tool 50 is threaded into abutment 10.

As shown in FIG. 7, tool 50 is rotated to unseat the Morse taper (bore portion 20a from abutment receiving portion 44) and release the abutment 10 from the implant 40.

Impression 70 containing tool 50 and abutment 10 is removed from the patient's mouth.

Figure 8:
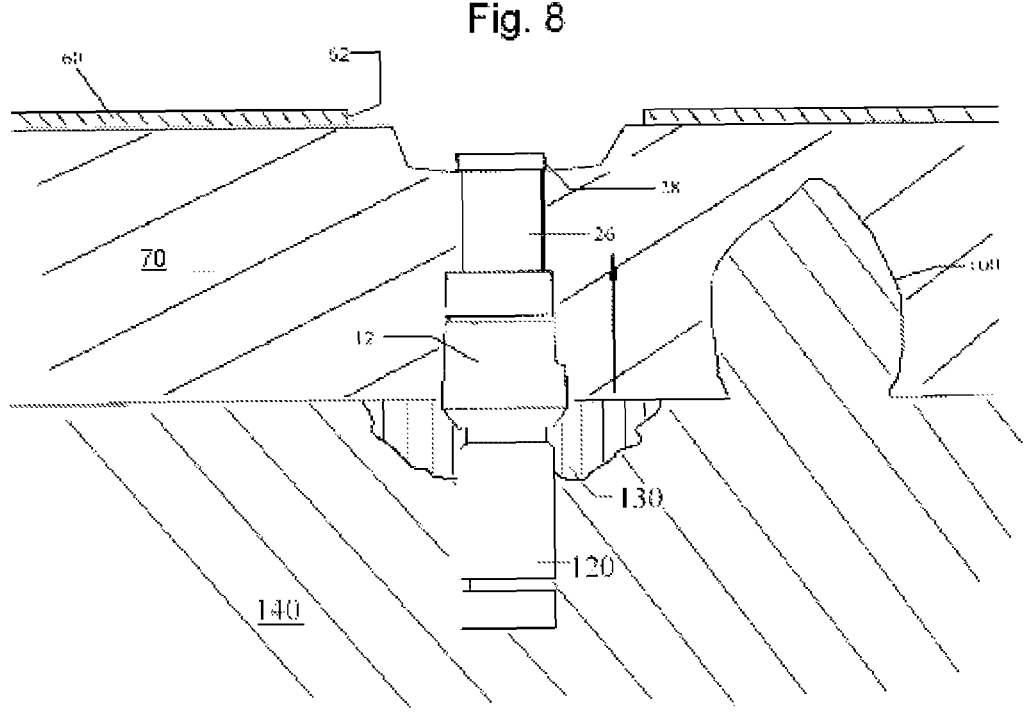
FIG. 8 is a view similar to FIG. 7 of the modeling step of the method of the invention with sectioned retainer.

Tool 50 is removed from the impression and the locking taper connection is activated between abutment 10 and an implant analog 120, shown in FIG. 8, with the help of insertion tool 30. Tool 30 is removed from abutment 10. Soft (130) and hard (140) model materials are poured into the impression 70.

Retaining member 24 is exposed from the overlying impression material 70 and is removed by being sectioned from the connector 26 or from abutment body 12, as described above. This can be accomplished by cutting the retaining member 24 around cutting line or area 28 using a dental burr.

The impression 70 with sectioned retaining member 24 is then removed from the model 130, 140 and is discarded. The pick-up abutment 10 remains connected to the implant analog 120 and thus accurate transfer of the abutment position is accomplished.

The method offers an accurate solution for indexing implants which utilize locking taper connections.

Screw Retained Pick-Up Abutment.

Figure 9:
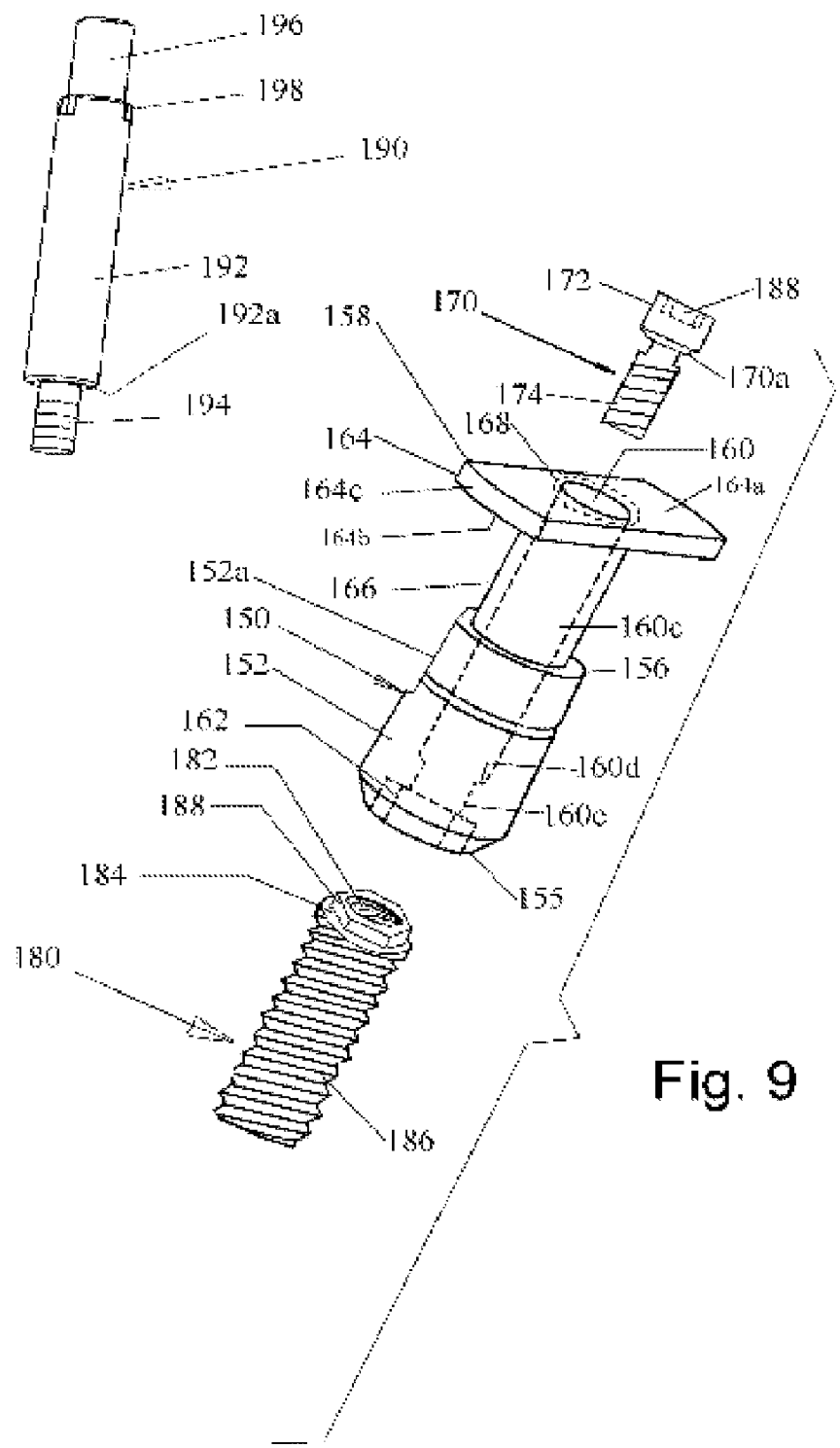
FIG. 9 is an exploded view of an embodiment of the invention for use with non-locking taper implant systems which utilize a retaining screw or a fastener to hold abutment and implant together.

FIG. 9 illustrates a pick-up abutment 150 for use with implant systems utilizing a retaining screw 170 for abutment to implant connection, the abutment having a body 152 with an outer peripheral wall that tapers from a large diameter location near its distal end 155, to a smaller diameter intermediate location 156. The body 152 may have a different shape, however. Pick-up abutment 150 has a proximal end 158 that is opposite its distal end 155, and an axial through bore 160 that extends all the way between the distal end 155 and proximal end 158 of the abutment 150.

The abutment 150 also has internal rotational implant indexing means 162 in the form of a hex located at the distal end 155, implant indexing means 162 may alternatively be in the form of an external hex or any other configuration that insures the correct relative rotational positions between the abutment 150 and the implant. Prosthesis anti-rotational means are provided by one or more flat surfaces 152a on the otherwise conical or cylindrical outer peripheral wall of body 152.

Figure 9A:
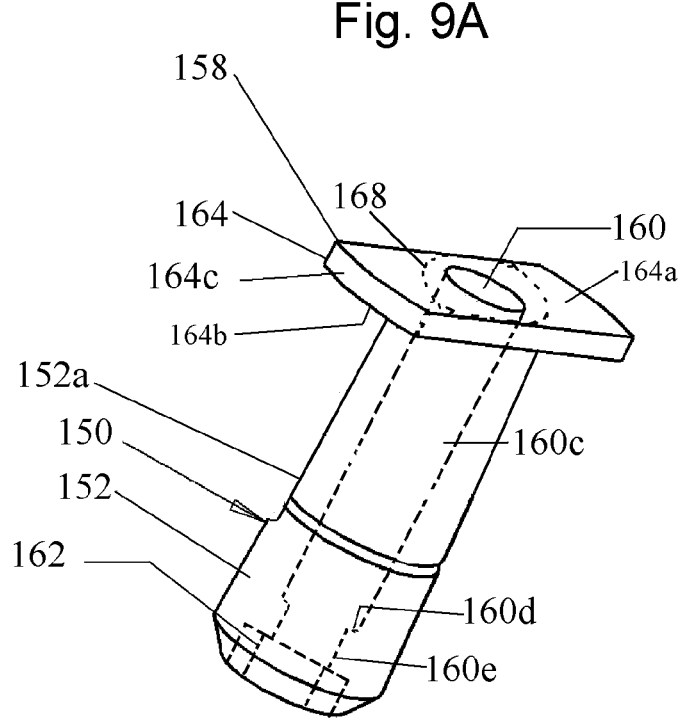
FIG. 9A is a side perspective view of a pick-up abutment embodiment.

The proximal end 158 of the abutment 150 has a retaining member 164 that is in the form of a disk or a plate or has another shape that is preferably asymmetrical. The retaining member 164 is connected to the body 152 of abutment 150, by a connector 166 that is cylindrical and has a smaller outside diameter then that of the body 152. The use of connector 166 is optional since retaining member 164 can be joined to, or be a part of, the abutment body 152 as shown in FIG. 9A. Connector 166 may have another shape and, in preferred embodiment, its transverse cross-sectional area, transverse to the axis of bore 160, is less than that of body 152. Retaining member 164 has upper (proximal) and lower (distal) surfaces 164a and 164b with an effective surface area transverse to the axis of bore 160 greater then the transverse cross-sectional area of connector 166. This results in good vertical stability of the entire abutment 150 in the impression material of an impression tray to be used in accordance with a method of the present invention, during an impression removal step of the method. Retaining member 164 may contain anti-rotational features, such as the rotationally asymmetrical shape shown, to prevent rotation in the impression material. Retaining member 164 also has a selected thickness between its upper and lower surfaces, so as not to become bent or distorted during impression removal. At the same time it should not be too thick so as to facilitate removal by cutting of the retaining member away from the connector 166, for example, using a dental burr, along a cutting line or area 168 at a later stage of the method. The cutting area 168 may be circular line in the retaining member 164 that corresponds to the diameter of the connector 166. Cutting area 168 may also correspond to cross-section of the abutment body 152 if retaining member 164 is joined directly to abutment body 152, as shown in FIG. 9A.

To this end the range of thickness for retaining member 164 is about 0.5 to 1.0 mm, or preferably about 0.7 to 0.8 mm. A preferred shape for the retaining member 164 is rectangular, and, in the embodiment shown, the rectangular shape has a longer dimension that is greater than the maximum diameter of the abutment body 152 with rounded ends 164c extending in the shorter dimension of the rectangle, the shorter dimension being between the diameter of the connector 166 and the minimum diameter of the abutment body 152.

The abutment 150 may be manufactured as one piece or be made of multiple permanently attached pieces.

Through axial bore 160 has rotational implant indexing means 162 at its distal or lower end, implant indexing means 162 correspond to abutment indexing means 188 of an abutment receiving portion 184 of an implant 180 to be used with the abutment. Axial bore 160 also includes a proximal or upper end bore portion 160c that is cylindrical and extends up along bore 160 to a proximal step-down in diameter at 160d.

FIG. 9 also illustrates a long fastener 190 which has an elongated body 192, a threaded implant engaging distal end 194 and a proximal end 196 with anti-rotational elements 198, such as circumferentially spaced, axial grooves at the top of body 192 for allowing application of torque using an appropriately shaped wrench or wrench engaging instrument. Threaded implant engaging distal end 194 has an external thread that corresponds in size and pitch to an internal thread 182 in abutment receiving portion 184 of an implant 180 shown also in FIG. 9.

Treaded distal end 194 has a smaller cross section and diameter then elongated body 192 to form a step-down in diameter at a distal step 192a. Elongated body 192 is also of a small enough diameter to slide into cylindrical bore portion 160c of bore 160 and treaded end 194 is long enough to reach the internal threads 182 of implant 180 until distal step 192a engages proximal step 160d of bore 160.

Implant 180 also includes a known anchoring portion 186, such as a thread to be screwed into a bore in the patient's jaw bone, as well as the abutment receiving portion 184 shaped to mate with indexing means 162 of the abutment 150 and a threaded internal bore 182 of a predetermined depth at the proximal or upper end of the implant 180.

Figure 10:
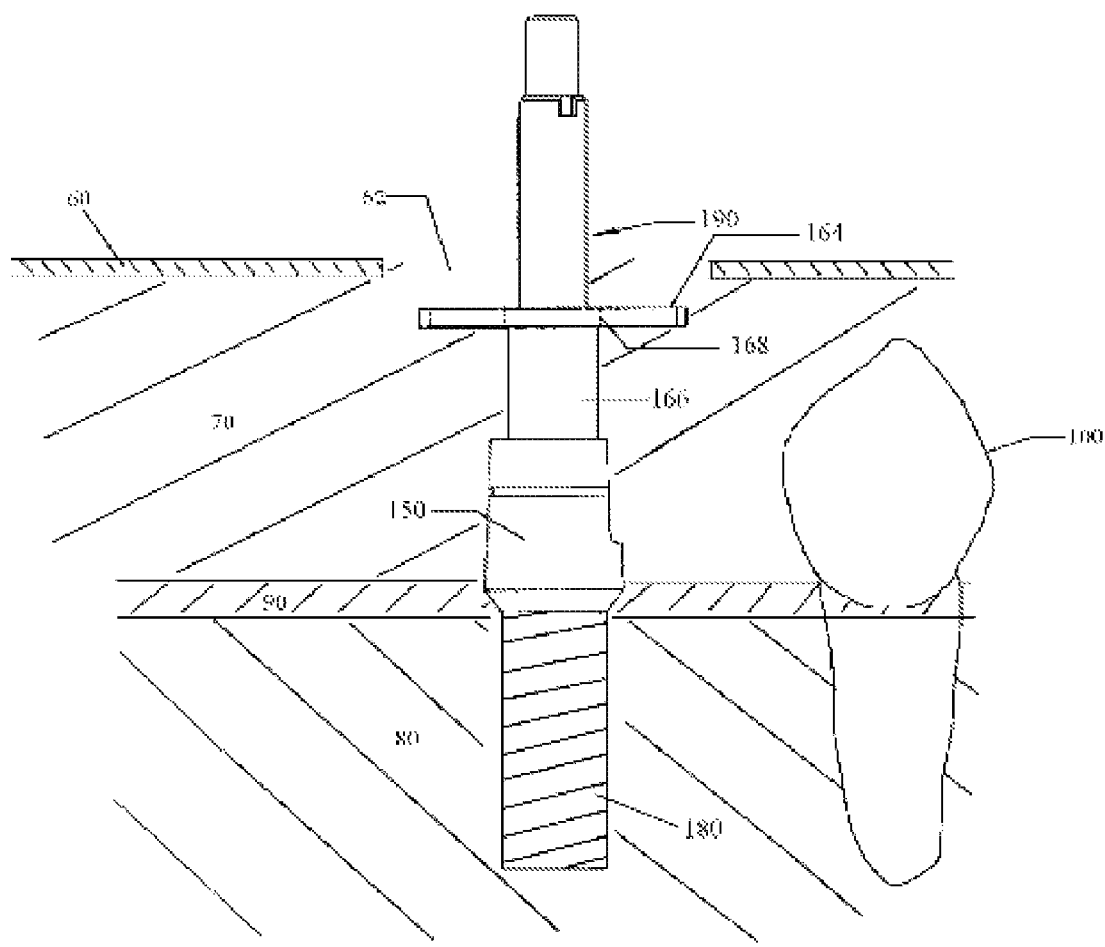
FIG. 10 is a side elevational view of an embodiment depicted in FIG. 9 with the arrangement in an impression material while practicing the method of the invention.

Screw Retained Pick-Up Abutment Method:

The method of taking the impression utilizing the screw retained pick-up abutment includes the stages of the method as follows:

The abutment 150 is connected to the implant 180 with a long fastener 190 as shown in FIG. 10.

An opening 62 in the tray 60 is provided to allow the fastener 190 to protrude through the impression material and the tray.

The impression tray with impression material 70 is inserted over the abutment 150 and surrounding dentition 100.

The fastener 190 is removed after impression is set. The impression 70 with abutment 150 is removed from the mouth.

Figure 11:
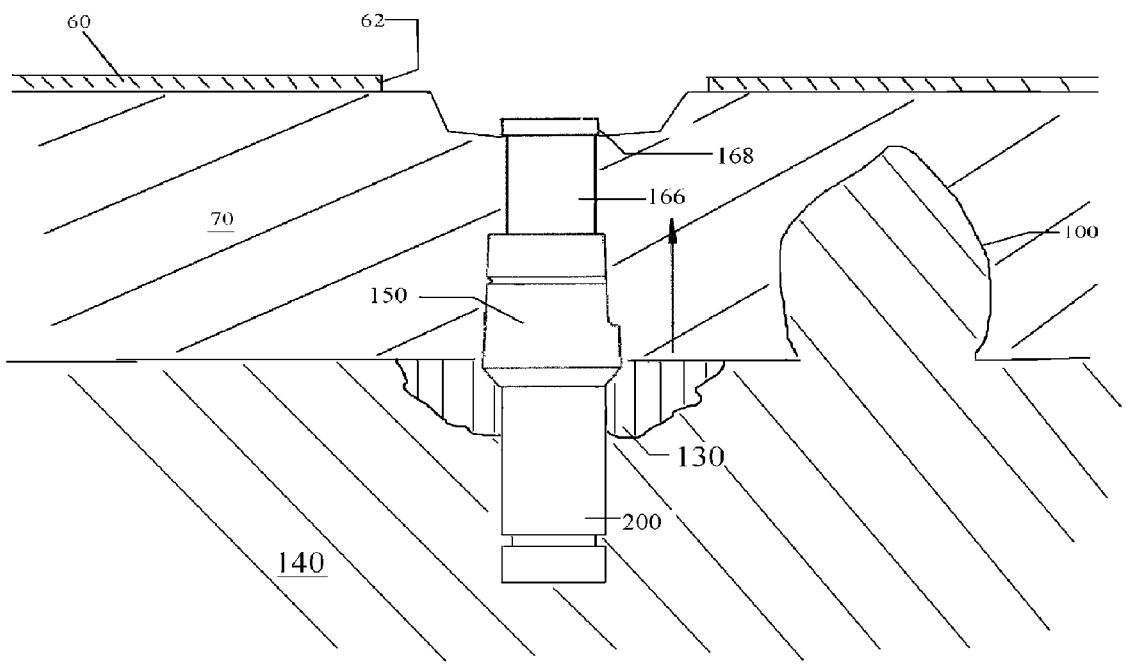
FIG. 11 is a side elevational view of the screw retained pick-up abutment arrangement of FIGS. 9 and 10 with the arrangement in a modeling material while practicing the method of the invention.

An implant analog 200 as shown in FIG. 11 is connected to the abutment 150 with long fastener 190 or, alternatively, with retaining screw 170 and model materials 130, 140 are poured into the impression.

All of these steps are similar to those of a standard open tray protocol. While pick-up coping (and the surrounding impression material) is removed from the implant analog after the model material hardens, the invention utilizes the following steps.

The retaining member 164 is exposed from the overlying impression material 70 and is removed, sectioned from the abutment (e.g. with a burr) along cutting area 168.

The impression with sectioned retaining member 164 is removed from the model and is discarded. Accurate transfer of the abutment position is accomplished.

The method offers many advantages over traditional closed and open tray methods. Some of these are:

(a) The fit between the abutment and the implant analog becomes irrelevant;

(b) The cost of the impression coping and the need to stock them is eliminated;

(c) The size difference between the abutment and the impression coping also becomes irrelevant, as well as the size difference between the implant and the implant analog; and (d) Distortion of the impression material, which is associated with closed tray method, is eliminated.

Pick-up abutment 150 can be used for the fabrication of cemented or screw retained prosthesis. If the pick-up abutment is used for fabrication of a screw retained restoration, it may become a part of the framework upon which the prosthesis is build.

FIG. 9 illustrates the abutment 150, the implant 180, retaining screw 170 and long fastener 190 that together form an overall arrangement of the present invention. Since various known implants may be used with a suitably adapted abutment 150 and retaining screw 110, the implant itself need not be a part of the arrangement of the invention.

While specific embodiments of the invention have been shown and described in detail to illustrate the application of the principles of the invention, it will be understood that the invention may be embodied otherwise without departing from such principles.

What is claimed is:

1. A dental implant abutment arrangement for use with a dental implant (40) having an anchoring portion (46) for anchoring in a jaw bone of a patient and an abutment receiving portion (44) opposite from the anchoring portion, the abutment receiving portion having an outer taper between 1 to 4 degrees for removably locking to a matching inner taper of an abutment and an internal implant thread (42) having diameter and a pitch, the arrangement comprising:

an abutment (10) having a body (12) with a peripheral wall and a distal end (15) for engagement with the implant, the abutment (10) having a proximal end (18) with a retaining member (24) to be removed prior to prosthesis fabrication connected to the body, the abutment (10) having a connector, the abutment having an axial bore (20) therethough extending between the distal and the proximal ends and having an axis, the retaining member (24) being rotationally asymmetrical about the axis and having an area transverse to the axis that is greater than a transverse area of the body so that the retaining member resists rotation and axial motion of the abutment in an impression material for taking a dental impression, the axial bore having a tapered distal bore portion (20a) with an inner taper for matching the outer taper of the abutment receiving portion, a cylindrical proximal bore portion (20c), and an intermediate threaded portion (20e) having a smaller diameter than that of the distal and proximal bore portions and a larger diameter than the internal thread (42) of the implant, the axial bore (20) having a distal step (20b) between the distal bore portion (20a) and a distal end of the threaded portion (20e), and a proximal step (20*d*) between the cylindrical proximal bore portion (20*c*) and a proximal end of the threaded portion (20*e*);

an insertion tool (30) having a body (32) with a diameter that is smaller than that of the cylindrical proximal bore portion (20*c*) so that the insertion tool can slide into the cylindrical proximal bore portion, a proximal end (36) with anti-rotation feature for engagement of the insertion tool (30) to rotate the insertion tool, and a threaded implant engaging end (34) having a diameter and pitch for threading into the internal implant thread (42), the threaded implant engaging end (34) being of a smaller diameter than a remainder of the insertion tool body (32) for defining a distal step (32*a*) around a proximal base of the threaded implant engaging end (34), the threaded implant engaging end (34) configured to be threaded into the internal thread of the implant for pulling the abutment toward the implant to removably lock the inner taper to the matching outer taper of the abutment receiving portion as the distal step (32*a*) of the insertion tool (30) engages the proximal step (20*d*) of the axial bore; and a removal tool (50) having a body (52) with a diameter that is smaller than that of the cylindrical proximal bore portion (20*c*) so that the removal tool can slide into the cylindrical proximal bore portion, a proximal end (56) with anti-rotation feature for engagement of the removal tool (50) to rotate the removal tool, and a threaded abutment engaging end (54) having a diameter and pitch for threading into the threaded portion (20*e*) of the axial bore, and having a diameter that is greater than the diameter of the internal thread (42) and a length that is sufficient so that the rotation of the removal tool (50) causes pushing of the implant away from the abutment to disengage the lock between the inner taper and the outer taper as the proximal end (56) of the removal tool engages the abutment receiving portion (44).

2. A dental implant abutment arrangement according to claim 1, wherein the retaining member (24) is rectangular with a longer dimension that is greater than a maximum diameter of the abutment body (12), and a shorter dimension that is less than a minimum diameter of the abutment body (12), a cutting area being an area in the retaining member that corresponds to a cross-section of the connector.

3. A dental implant abutment arrangement according to claim 1, wherein the retaining member (24) is rectangular with a longer dimension that is greater than a maximum diameter of the abutment body (12), and a shorter dimension that is less than a minimum diameter of the abutment body (12), a cutting area being an area in the retaining member that corresponds to a cross-section of the connector, and a thickness parallel to the bore axis that is sufficient so as not to become bent during impression removal and not so thick so as to facilitate removal by cutting of the retaining member away along a cutting area.

4. A dental implant abutment arrangement according to claim 1, wherein the retaining member (24) is a rectangular plate with a longer dimension that is greater than a maximum diameter of the abutment body (12), and a shorter dimension that is less than a minimum diameter of the abutment body (12), the cutting area being an area in the retaining member that corresponds to a cross-section of the connector, the retaining member having a thickness parallel to the bore axis between 0.5 to 1.0 mm so that the thickness is sufficient so as not to become bent during impression removal and not so thick so as to facilitate removal by cutting of the retaining member away along the cutting area.

5. A dental implant abutment arrangement according to claim 1, wherein the abutment body (12) has a maximum diameter (14) near the distal end (15) and a minimum diameter (16) near the connector (26) that is larger than the diameter of the connector.

6. A dental implant abutment arrangement according claim 1, wherein the abutment manufactured as one-piece or made of multiple permanently attached pieces.

* * * * *